(12) United States Patent
Robinson (10) Patent No.: US 10,993,511 B1
(45) Date of Patent: May 4, 2021

(54) THERAPEUTIC BRACELET

(71) Applicant: Randall B. Robinson, Madison Heights, VA (US)

(72) Inventor: Randall B. Robinson, Madison Heights, VA (US)

( * ) Notice: Subject to any disclaimer, the term of this patent is extended or adjusted under 35 U.S.C. 154(b) by 273 days.

(21) Appl. No.: 16/198,845

(22) Filed: Nov. 22, 2018

Related U.S. Application Data

(60) Provisional application No. 62/589,637, filed on Nov. 22, 2017.

(51) Int. Cl.
| | |
|---|---|
| *A44C 5/00* | (2006.01) |
| *H01R 13/652* | (2006.01) |
| *H01R 24/28* | (2011.01) |
| *H01R 13/68* | (2011.01) |
| *A61N 1/14* | (2006.01) |
| *H01R 103/00* | (2006.01) |

(52) U.S. Cl.
CPC ............ *A44C 5/0023* (2013.01); *A44C 5/003* (2013.01); *H01R 13/652* (2013.01); *H01R 13/68* (2013.01); *H01R 24/28* (2013.01); *A61N 1/14* (2013.01); *H01R 2103/00* (2013.01); *H01R 2201/12* (2013.01)

(58) Field of Classification Search
CPC .... A44C 5/0023; A44C 5/003; H01R 13/652; H01R 13/68; H01R 24/28; H01R 2103/00; H01R 2201/12; A61N 1/14
USPC .......................................................... 361/220
See application file for complete search history.

(56) References Cited

U.S. PATENT DOCUMENTS

| | | | | |
|---|---|---|---|---|
| 4,373,175 A | * | 2/1983 | Mykkanen | ............... A61N 1/14 361/212 |
| 4,854,319 A | * | 8/1989 | Tobin | ....................... A61F 7/10 607/109 |
| 6,683,779 B2 | | 1/2004 | Ober | |
| 6,772,445 B2 | | 8/2004 | Yeager | |
| 7,209,791 B2 | | 4/2007 | Odon | |
| 7,259,954 B2 | * | 8/2007 | Edstrom | ................. H05F 3/025 361/212 |
| 7,724,491 B2 | | 5/2010 | Oder et al. | |
| 7,837,719 B2 | | 11/2010 | Brogan et al. | |

(Continued)

FOREIGN PATENT DOCUMENTS

| | | |
|---|---|---|
| CN | 202425639 | 9/2012 |
| CN | 202942545 | 5/2013 |

(Continued)

OTHER PUBLICATIONS www.sukiusa.com.

*Primary Examiner* — Kevin J Comber
(74) *Attorney, Agent, or Firm* — Shaddock Law Group, PC (57) ABSTRACT

A therapeutic bracelet, including a bracelet body having one or more cavities formed therein; a catalyst solution contained within each of the one or more cavities; an electrical connector electrically attached or coupled to the bracelet body; a connecting cord electrically attached or coupled to the electrical connector; and a plug assembly, wherein the plug assembly includes a "live" pin or blade, a neutral pin or blade, and an earth/ground pin or blade, wherein the "live" pin or blade and the neutral pin or blade are electrically disconnected from the connecting cord and the earth/ground pin or blade, and wherein the earth/ground pin or blade is electrically connected to the connecting cord.

20 Claims, 6 Drawing Sheets

(56) References Cited

U.S. PATENT DOCUMENTS

| | | | |
|---|---|---|---|
| 7,905,111 B2 | 3/2011 | Saltz | |
| D710,737 S | 8/2014 | West | |
| 8,819,988 B2 * | 9/2014 | Corsi | ........................ A01G 7/04 47/1.3 |
| 9,578,135 B2 | 2/2017 | Horgan | |
| D780,613 S | 3/2017 | Shaukat et al. | |
| 2011/0139823 A1 | 6/2011 | Staudt | |
| 2013/0158425 A1 | 6/2013 | Kaye et al. | |
| 2014/0313040 A1 | 10/2014 | Wright, Sr. | |
| 2016/0166830 A1 | 6/2016 | Avent et al. | |

FOREIGN PATENT DOCUMENTS

| | | |
|---|---|---|
| CN | 203016017 | 6/2013 |
| CN | 105105910 | 12/2015 |
| FR | 2300517 | 10/1976 |
| FR | 2601595 | 1/1988 |
| JP | 11127920 | 5/1999 |

\* cited by examiner

THERAPEUTIC BRACELET

CROSS-REFERENCE TO RELATED APPLICATIONS

This patent application claims the benefit of U.S. Patent Application Ser. No. 62/589,637, filed Nov. 22, 2017, the entire disclosure of which is incorporated herein by reference.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

NOTICE OF COPYRIGHTED MATERIAL

The disclosure of this patent document contains material that is subject to copyright protection. The copyright owner has no objection to the reproduction by anyone of the patent document or the patent disclosure, as it appears in the Patent and Trademark Office patent file or records, but otherwise reserves all copyright rights whatsoever. Unless otherwise noted, all trademarks and service marks identified herein are owned by the applicant.

BACKGROUND OF THE PRESENT DISCLOSURE

1. Field of the Present Disclosure

The present disclosure relates generally to the field of bracelets. More specifically, the presently disclosed systems, methods, and/or apparatuses relates to a personal grounding, therapeutic bracelet.

2. Description of Related Art

People sometimes wear bracelets or other items constructed of certain materials as a form of alternative medicine to improve the person's overall well-being. For example, some people where bracelets having one or more magnets embedded therein as a tool for magnetic therapy.

Any discussion of documents, acts, materials, devices, articles, or the like, which has been included in the present specification is not to be taken as an admission that any or all of these matters form part of the prior art base or were common general knowledge in the field relevant to the present disclosure as it existed before the priority date of each claim of this application.

BRIEF SUMMARY OF THE PRESENT DISCLOSURE

However, current therapeutic or other bracelets do not act to reconnect man with the earth through an electrical connection. The therapeutic bracelet of the present disclosure, among other things, reconnects man with the earth (as was the condition with early man, prior to the application of foot coverings and separation through housing, sidewalks, etc.) through an electrical connection consisting of a fluid catalyst solution filled conductive bracelet (or fluid catalyst solution filled bracelet insert), a conductive cord, and an earth (or ground) connection.

The therapeutic bracelet of the present disclosure is intended to help restore electrical balance to the "system" of man-and-environment as was originally designed. Man's advancement and understanding of technology over the millennia is undeniable. However, man's developments have ultimately reduced personal connection and interaction with the earth. The therapeutic bracelet's overarching premise is that man was made from earth and to be in contact with it. The therapeutic bracelet seeks to solve the negative impact caused by our current state of disconnectedness as a result of housing, sidewalks, automobiles, clothing, etc. Modern life has essentially "opened" the electrical circuit that was designed by God.

The man-and-environment system comprises the electrical, chemical, mechanical, and even spiritual aspects of all that we know. The therapeutic bracelet positively impacts the human experience through further engagement (or re-engagement) of human beings with the earth. The therapeutic bracelet operates on a basic elemental approach—that the usage of a basic elemental conductor (e.g., copper or another electrically conductive material), a conductive catalyst solution (e.g., some form of water or other liquid solution, air, gas, etc., or combinations thereof) and earth helps restore fundamental interactions such as proper electrical balance and current flow between man and the earth.

By appropriately reconnecting the human body to the earth (or a ground), a number of health benefits can potentially be realized, including, for example (but not limited to), improved relaxation, reduced inflammation, reduced chronic pain, improved joint mobility, deeper sleep, improved circulation, reduced illness severities and durations, heightened energy, more rapid hair and nail growth, improved excretory functions, and improved mental clarity.

These improvements and health benefits stem from the fact that electrically coupling a human with the earth facilitates the discharge of routine electrical buildup that results from inescapable aspects of modern daily human life, such as RF (radio frequency), EMF (electro-motive force), static electricity, etc. Removal of this electrical buildup eliminates interference in the human body and literally resets the human body's electrical system to perform as designed.

In various exemplary, non-limiting embodiments, the therapeutic bracelet of the presently disclosed systems, methods, and/or apparatuses comprises a fluid catalyst solution contained within a conductive bracelet. Integrated as a simple electrical assembly, the therapeutic bracelet of the present disclosure comprises a bracelet body, a catalyst solution contained within one or more cavities formed within the bracelet body, an electrical connector, a conductive connecting cord, which may optionally contain a protective circuit breaker, such as, for example, a fuse, and a plug assembly. These components are configured such that the bracelet body containing the fluid catalyst solution is attached, via an electrical connector, to a connecting cord that is terminated with a plug assembly designed to safely interface to a properly wired North American, home-style 110 VAC electrical outlet. The plug assembly is intended to be plugged into an electrical outlet to provide a human connection (through the bracelet) to the earth (through the earth/grounding pin or blade).

In various exemplary, non-limiting embodiments, the therapeutic bracelet of the presently disclosed systems, methods, and/or apparatuses comprises a bracelet body having one or more cavities formed therein; a catalyst solution contained within one or more cavities; an electrical connector electrically attached or coupled to the bracelet body; a connecting cord electrically attached or coupled to the electrical connector; and a plug assembly, wherein the plug assembly includes a "live" pin or blade, a neutral pin or blade, and an earth/ground pin or blade, wherein the "live" pin or blade and the neutral pin or blade are electrically disconnected from the connecting cord and the earth/ ground pin or blade, and wherein the earth/ground pin or blade is electrically connected to the connecting cord.

In certain exemplary, nonlimiting embodiments, each of the cavities may be in fluid communication with each other cavity.

In certain exemplary, nonlimiting embodiments, the plug assembly is capable of interfacing with an electrical outlet.

In certain exemplary, nonlimiting embodiments, the plug assembly is capable of interfacing with a North American-style 110 VAC electrical outlet.

In certain exemplary, nonlimiting embodiments, the plug assembly is capable of interfacing with any Type A, Type B, Type C, Type D, Type E, Type F, Type G, Type H, Type I, Type J, Type K, Type L, Type M, Type N, or Type O electrical outlet.

In certain exemplary, nonlimiting embodiments, if the electrical plug assembly is plugged into an electrical outlet, the earth/ground pin or blade is electrically connected to the earth/ground of the electrical outlet.

In certain exemplary, nonlimiting embodiments, the therapeutic bracelet includes a fuse assembly attached or coupled between the cord and the plug assembly.

In various exemplary, non-limiting embodiments, the therapeutic bracelet of the presently disclosed systems, methods, and/or apparatuses comprises a bracelet body having one or more cavities formed therein; a catalyst solution contained within one or more cavities; a connecting cord electrically attached or coupled to the bracelet body; and a plug assembly, wherein the plug assembly includes a "live" pin or blade, a neutral pin or blade, and an earth/ ground pin or blade, wherein the "live" pin or blade and the neutral pin or blade are electrically disconnected from the connecting cord and the earth/ground pin or blade, and wherein the earth/ground pin or blade is electrically connected to the connecting cord.

In various exemplary, non-limiting embodiments, the therapeutic bracelet of the presently disclosed systems, methods, and/or apparatuses comprises a bracelet body having at least one cavity formed therein; a catalyst solution contained within the at least one cavity; a connecting cord electrically attached or coupled to the bracelet body; and a plug assembly, wherein the plug assembly includes a "live" pin or blade, a neutral pin or blade, and an earth/ground pin or blade, wherein the "live" pin or blade and the neutral pin or blade are nonconductive, and wherein the earth/ground pin or blade is electrically connected to the connecting cord.

Accordingly, the presently disclosed systems, methods, and/or apparatuses separately and optionally provide therapeutic bracelets that allow a user to reconnect the user's body to an earth/ground.

The presently disclosed systems, methods, and/or apparatuses separately and optionally provide therapeutic bracelets that provide various health well-being benefits to the user.

The presently disclosed systems, methods, and/or apparatuses separately and optionally provide therapeutic bracelets that can be easily utilized by a user.

These and other aspects, features, and advantages of the presently disclosed systems, methods, and/or apparatuses are described in or are apparent from the following detailed description of the exemplary, non-limiting embodiments of the presently disclosed systems, methods, and/or apparatuses and the accompanying figures. Other aspects and features of embodiments of the presently disclosed systems, methods, and/or apparatuses will become apparent to those of ordinary skill in the art upon reviewing the following description of specific, exemplary embodiments of the presently disclosed systems, methods, and/or apparatuses in concert with the figures. While features of the presently disclosed systems, methods, and/or apparatuses may be discussed relative to certain embodiments and figures, all embodiments of the presently disclosed systems, methods, and/or apparatuses can include one or more of the features discussed herein. Further, while one or more embodiments may be discussed as having certain advantageous features, one or more of such features may also be used with the various embodiments of the systems, methods, and/or apparatuses discussed herein. In similar fashion, while exemplary embodiments may be discussed below as device, system, or method embodiments, it is to be understood that such exemplary embodiments can be implemented in various devices, systems, and methods of the presently disclosed systems, methods, and/or apparatuses.

Any benefits, advantages, or solutions to problems that are described herein with regard to specific embodiments are not intended to be construed as a critical, required, or essential feature(s) or element(s) of the presently disclosed systems, methods, and/or apparatuses or the claims.

BRIEF DESCRIPTION OF THE SEVERAL VIEWS OF THE DRAWINGS

As required, detailed exemplary embodiments of the presently disclosed systems, methods, and/or apparatuses are disclosed herein; however, it is to be understood that the disclosed embodiments are merely exemplary of the presently disclosed systems, methods, and/or apparatuses that may be embodied in various and alternative forms, within the scope of the presently disclosed systems, methods, and/or apparatuses. The figures are not necessarily to scale; some features may be exaggerated or minimized to illustrate details of particular components. Therefore, specific structural and functional details disclosed herein are not to be interpreted as limiting, but merely as a basis for the claims and as a representative basis for teaching one skilled in the art to employ the presently disclosed systems, methods, and/or apparatuses.

The exemplary embodiments of the presently disclosed systems, methods, and/or apparatuses will be described in detail, with reference to the following figures, wherein like reference numerals refer to like parts throughout the several views, and wherein.

DETAILED DESCRIPTION OF EXEMPLARY EMBODIMENTS OF THE PRESENT DISCLOSURE

For simplicity and clarification, the design factors and operating principles of the therapeutic bracelet according to the presently disclosed systems, methods, and/or apparatuses are explained with reference to various exemplary embodiments of a therapeutic bracelet according to the presently disclosed systems, methods, and/or apparatuses. The basic explanation of the design factors and operating principles of the therapeutic bracelet is applicable for the understanding, design, and operation of the therapeutic bracelet of the presently disclosed systems, methods, and/or apparatuses. It should be appreciated that the therapeutic bracelet can be adapted to many applications where a therapeutic bracelet can be used.

As used herein, the word "may" is meant to convey a permissive sense (i.e., meaning "having the potential to"), rather than a mandatory sense (i.e., meaning "must"). Unless stated otherwise, terms such as "first" and "second" are used to arbitrarily distinguish between the exemplary embodiments and/or elements such terms describe. Thus, these terms are not necessarily intended to indicate temporal or other prioritization of such exemplary embodiments and/or elements.

The term "coupled", as used herein, is defined as connected, although not necessarily directly, and not necessarily mechanically. The terms "a" and "an" are defined as one or more unless stated otherwise.

Throughout this application, the terms "comprise" (and any form of comprise, such as "comprises" and "comprising"), "have" (and any form of have, such as "has" and "having"), "include", (and any form of include, such as "includes" and "including") and "contain" (and any form of contain, such as "contains" and "containing") are used as open-ended linking verbs. It will be understood that these terms are meant to imply the inclusion of a stated element, integer, step, or group of elements, integers, or steps, but not the exclusion of any other element, integer, step, or group of elements, integers, or steps. As a result, a system, method, or apparatus that "comprises", "has", "includes", or "contains" one or more elements possesses those one or more elements but is not limited to possessing only those one or more elements. Similarly, a method or process that "comprises", "has", "includes" or "contains" one or more operations possesses those one or more operations but is not limited to possessing only those one or more operations.

It should also be appreciated that the terms "therapeutic" and "therapeutic bracelet" are used for basic explanation and understanding of the operation of the systems, methods, and apparatuses of the presently disclosed systems, methods, and/or apparatuses. Therefore, the terms "therapeutic" and "therapeutic bracelet" are not to be construed as limiting the systems, methods, and apparatuses of the presently disclosed systems, methods, and/or apparatuses.

Turning now to the appended drawing figures, FIGS. 1-12 illustrate certain elements, aspects, and/or variants of an exemplary embodiment of a therapeutic bracelet 100 and a therapeutic bracelet 100', according to the presently disclosed systems, methods, and/or apparatuses. In illustrative, non-limiting embodiment(s), the therapeutic bracelet 100 comprises at least some of a bracelet body 103, a catalyst solution 110, an electrical connector 120, a connecting cord 130, which may optionally include a protective circuit breaker, such as a fuse 155 contained within a fuse assembly 150, and a plug assembly 140.

In various exemplary, nonlimiting embodiments, the bracelet body 103 is formed of an electrically conductive material, such as, for example, copper. As illustrated most clearly in FIG. 1, the bracelet body 103 is not comprised of a completely closed circle nor is the bracelet body 103 connected to itself at its terminal ends 104. Rather, the terminal ends 104 are opened, and may optionally be offset from one another as partially shown in FIG. 2, to facilitate easy installation onto a human wrist. Thus, it should be appreciated that the terminal ends 104 may be aligned or offset relative to one another.

The bracelet 100 can be formed to essentially any length (and overall opening diameter) to accommodate various wrist sizes. Also, the bracelet body 103 may be semi-adjustable; allowing the bracelet body 103 to be opened and closed slightly through bending during installation and/or removal, without significant distortion or damage. The degree or angle of allowable opening is a design choice, based upon the desired functionality of the bracelet 100.

Figure 4A:
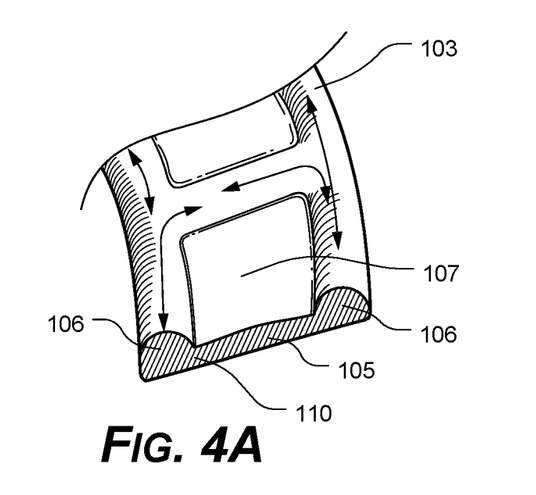
FIG. 4A illustrates a partial cross-sectional view of an exemplary bracelet body of an exemplary embodiment of the therapeutic bracelet, according to the presently disclosed systems, methods, and/or apparatuses.
Figure 4B:
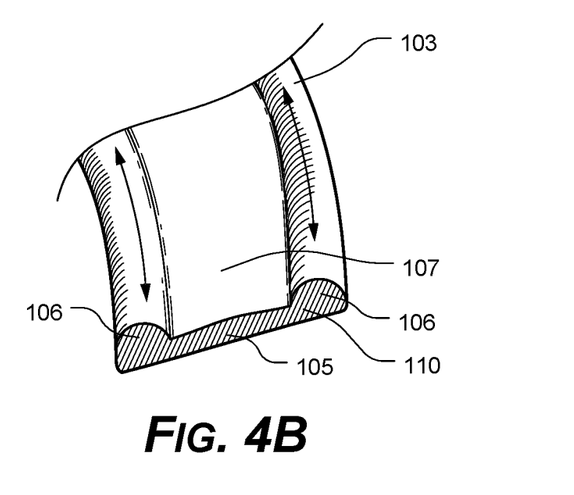
FIG. 4B illustrates a partial cross-sectional view of an exemplary bracelet body of an exemplary embodiment of the therapeutic bracelet, according to the presently disclosed systems, methods, and/or apparatuses.

As illustrated most clearly in FIGS. 4A and 4B, a bracelet body 103 is formed to include one or more internal cavities 105. Each of the cavities 105 may be formed by crimping, pressing, or bending the material used to form portions of the bracelet body 103. The bends or crimps form indentions or depressions 107 in the bracelet body 103, creating one or more cavities 105, within the hollow interior of the bracelet body 103. Alternatively, the bracelet body 103 may be formed as an integral unit including one or more internally formed cavities 105.

Various exemplary, nonlimiting embodiments, the exterior of the bracelet body 103 may optionally include patterns, etchings, attachments, or other surface preparations to promote or facilitate use of the bracelet 100 or to foster improved performance, comfort, or aesthetic appeal. These patterns, etchings, attachments, or other surface preparations may also provide some means of decoration or personalization to promote use or to prevent confusion. The bracelet body 103 may optionally include a fastener or other closing mechanism such as a clip, latch, or band to ensure that the therapeutic bracelet 100 remains secure on a user's wrist. The fastener or other closing mechanism may optionally be adjustable through various methods such as holes, elastic, or multiple latch points.

As illustrated most clearly in FIG. 4A and FIG. 4B, channels 106 may be formed by or between each of the cavities 105, such that each cavity 105 is in fluid communication with one or more other cavities 105 to form an internal fluid flow network of the therapeutic bracelet 100. In certain exemplary embodiments, each cavity 105 may be joined to each of the other cavities 105, via one or more channels 106. Alternatively, groups of cavities 105 may be joined, via one or more channels 106, resulting in one or more groups of interconnected channels 106 or cavities 105 and/or one or more groups of isolated channels 106 or cavities 105.

In certain exemplary embodiments, at least some channels 106 are formed along the length of the bracelet body 103, along or proximate each outer edge of the bracelet body 103. One or more cross channels 106 may optionally be formed at various angles to the length of the bracelet body 103, joining at least certain of the channels 106.

The internal fluid flow network of the therapeutic bracelet 100 may optionally be formed by clearly defined geometry such as channels 106 per inch, or certain connected channels 106 versus isolated channels 106, or other configurations such as a more open, less restrictive flow space.

In certain exemplary embodiments, the bracelet body 103 is constructed of a flattened copper tube, formed with an internal network of channels 106 and cavities 105. Other embodiments of the therapeutic bracelet 100 might include a different diameter copper tube or a different pliable, conductive metal such as brass or aluminum.

The internal channels 106 and/or cavities 105 of the bracelet body 103 are filled (or are at least partially filled) with a conductive catalyst solution 110. The conductive catalyst solution 110 may optionally comprise different fluids, gases, chemicals, etc. For example, the catalyst solution 110 may optionally comprise tap water, spring water, distilled water, de-ionized water, alcohol, oxygen, hydrogen, air, or the like. Additives or combinations of such with specific chemical makeups may be used to induce, enhance, or otherwise assist the control of electron transfer from the human wrist or body to the earth (including negative or reversed flow patterns) and/or offer other potential benefits. Additives such as dyes may optionally be included to highlight leaks. In certain exemplary, nonlimiting embodiments, oils or other additives, such as, for example, essential oils, may optionally be added to the catalyst solution 110 to promote certain other benefits.

The one or more cavities 105 are hermetically or otherwise sealed so that the conductive fluid or catalyst solution 110 is unable to escape from the cavities 105 and channels 106 of the bracelet body 103. The cavities 105 and channels 106 may be sealed by sealed terminal ends 104 of the bracelet 100 to prevent leakage of the catalyst solution 110 from the interior of the bracelet body 103. This sealing may optionally be facilitated through various means such as crimping, gluing, brazing, soldering, capping, etc.

The internal network of connected channels 106 and/or cavities 105 include enough flow space to facilitate movement of the catalyst solution 110, within the channels 106 and/or cavities 105, due to inertia, expansion, contraction from thermal cycling, etc.

The electrical connector 120 is attached or coupled to the bracelet body 103 so as to ensure electrical connection and electrical conductivity between the bracelet body 103 and the connecting cord 130. As the sealed integrity of the internal channels 106 and/or cavities 105 of the bracelet body 103 must be preserved to prevent leakage of the catalyst solution 110, certain exemplary embodiments may optionally utilize various electrical connection methods to prevent piercing of the bracelet body 103, such as direct braze, solder, wire wrap, crimp, etc. Such electrical connections may be fixed or permanent direct connections to the bracelet body 103 or may be detachable, such as using a socket, lug, receptacle, or other style electrical connector 120.

If the electrical connector 120 is attached or coupled in an area proximate a cavity 105 and/or channel 106, the electrical connector 120 may optionally be attached or coupled to the bracelet body 103 in a manner that avoids piercing of the bracelet body 103 by brads, screws, etc. In certain exemplary embodiments, as illustrated most clearly in FIGS. 1-3, the electrical connector 120 comprises a flattened portion of copper or other tubular material that is at least partially formed or wrapped around a portion of the bracelet body 103. The flattened portion of material is conductively attached or coupled to the bracelet body 103.

Figure 5:
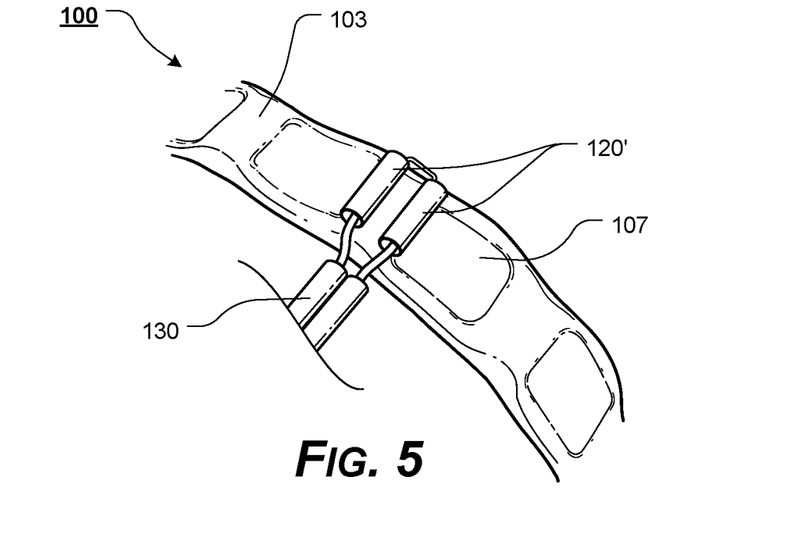
FIG. 5 illustrates a variant embodiment view of an exemplary connecting cord attachment of an exemplary embodiment of the therapeutic bracelet, according to the presently disclosed systems, methods, and/or apparatuses.

As illustrated, for example, in FIG. 5, an electrical connector 120' may optionally comprise one or more electrical connectors 120' attached or coupled to the bracelet body 103. The one or more cords of the conductive wire 130 are attached or coupled to or within portions of the electrical connector 120'.

Figure 6:
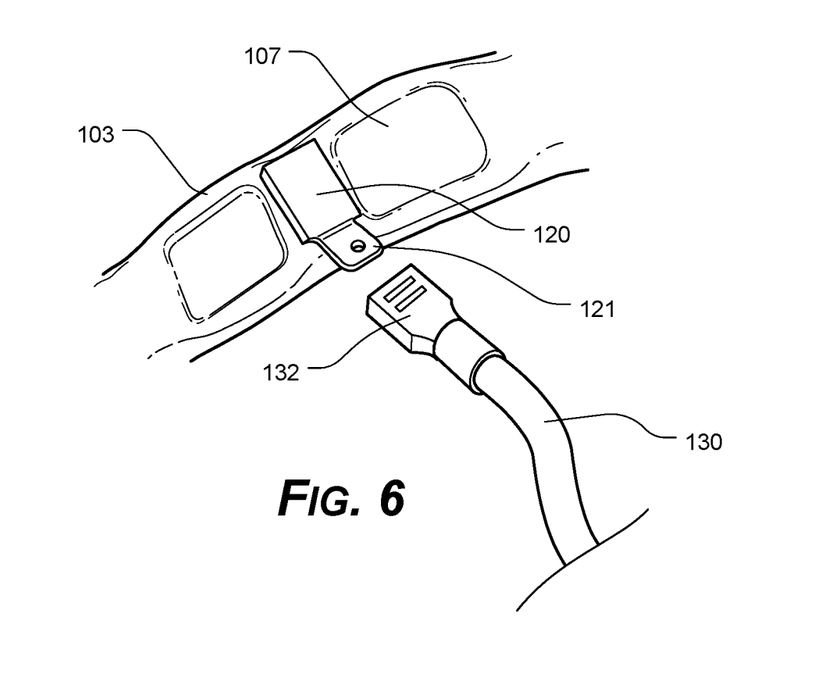
FIG. 6 illustrates a variant embodiment view of an exemplary electrical connector and connecting cord of exemplary embodiment of the therapeutic bracelet, according to the presently disclosed systems, methods, and/or apparatuses.

As illustrated, for example, in FIG. 6, the electrical connector 120 may optionally comprise at least one fixed or detachable male spade connector 121, which may be attached or coupled to a corresponding female spade connector 132 attached or coupled to the connecting cord 130. Alternatively, it should be appreciated that a female spade connector may optionally be formed as a portion of the electrical connector 120 and a male spade connector may optionally be attached or coupled to the connecting cord 130. Alternate electrical connections may include direct solder or braze of the electrical connector 120 to the bracelet body 103, wire wrapping, etc. It should be appreciated that attachment or coupling of the electrical connector 120 and connecting cord 130 to the bracelet body 103 is done so as to ensure a robust connection of high electrical integrity.

Figure 7:
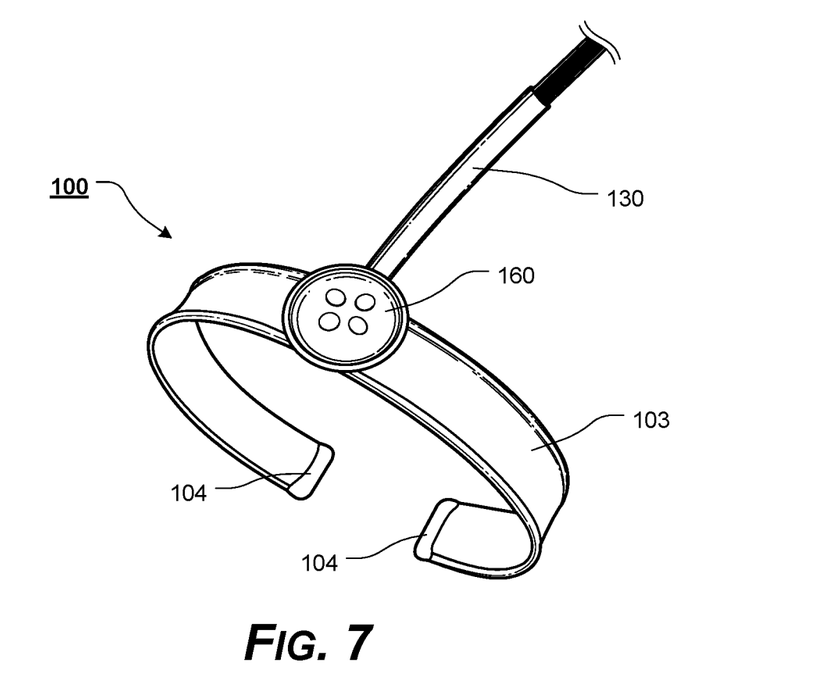
FIG. 7 illustrates a perspective view of certain elements or components of an exemplary embodiment of a therapeutic bracelet, according to the presently disclosed systems, methods, and/or apparatuses.

As illustrated, for example, in FIG. 7, various decorations and/or ornamentations 160 may be included as part of the therapeutic bracelet 100. If included, the decorations and/or ornamentations 160 may be permanently or removably attached or coupled to the bracelet body 103 and/or the electrical connector 120 of the therapeutic bracelet 100.

The connecting cord 130 is electrically attached or coupled to the electrical connector 120. As illustrated most clearly in FIG. 9, the connecting cord 130 may optionally include a length of two-conductor zip-style (i.e., two conductors with connected insulation across their lengths) electrical cord connected between the electrical connector 120 and the plug assembly 140.

The connecting cord 130 may comprise one or more conductive wires having desired electrical conductivity characteristics. For example, the conductive wires may be formed of single-strand or braided copper, silver, aluminum, or some combination thereof. A specific gauge (e.g., 18, 16, 14, 12, 10, etc.), weight, or length of connecting cord 130 may be used or a configuration that includes a single wire, shielded cable, or other form of wire to promote optimal performance and durability. The connecting cord 130 and/or any associated connections may include various strain reliefs such as knots, loops, heat shrink tubing, etc. to promote effectiveness and durability. Any such strain reliefs may be designed and placed specifically and uniquely for the therapeutic bracelet 100 of the present disclosure.

Figure 1:
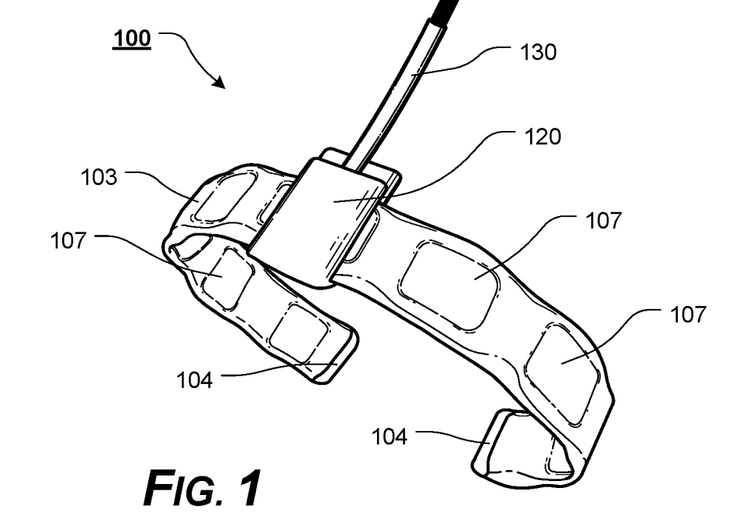
FIG. 1 illustrates a perspective view of certain elements or components of an exemplary embodiment of a therapeutic bracelet, according to the presently disclosed systems, methods, and/or apparatuses.
Figure 2:
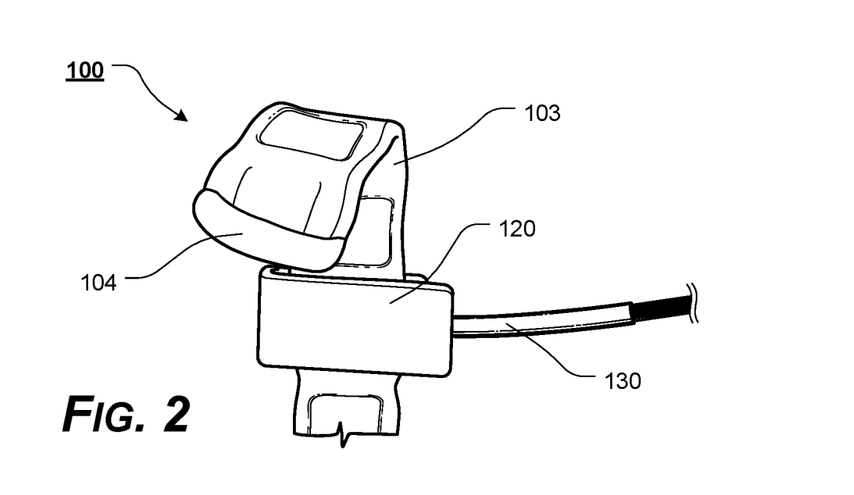
FIG. 2 illustrates a more detailed view of certain elements or components of an exemplary embodiment of the therapeutic bracelet, according to the presently disclosed systems, methods, and/or apparatuses.
Figure 3:
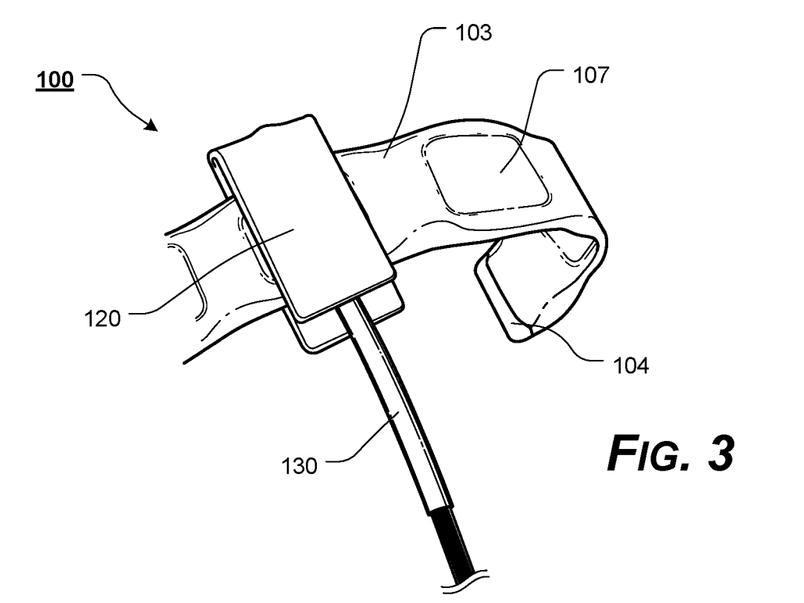
FIG. 3 illustrates a more detailed view of certain elements or components of an exemplary embodiment of the therapeutic bracelet, according to the presently disclosed systems, methods, and/or apparatuses.

In various exemplary embodiments, the connecting cord 130 is conductively attached or coupled to the bracelet body 103 in various ways, such as direct solder or braze or crimping through a short copper tube that is formed around and electrically attached or coupled to the bracelet body 103, as illustrated, for example, in FIGS. 1-3. Attachment methods may range from a general epoxy to very specific epoxies (e.g., marine grade epoxy) or other attachment methods such as soldering, brazing, etc. Certain surface preparations (e.g., scoring, etching, etc.) may be incorporated to enhance electrical conductivity, conductive performance, and/or durability between the connecting cord 130, the electrical connector 120, and/or the bracelet body 103.

Figure 8:
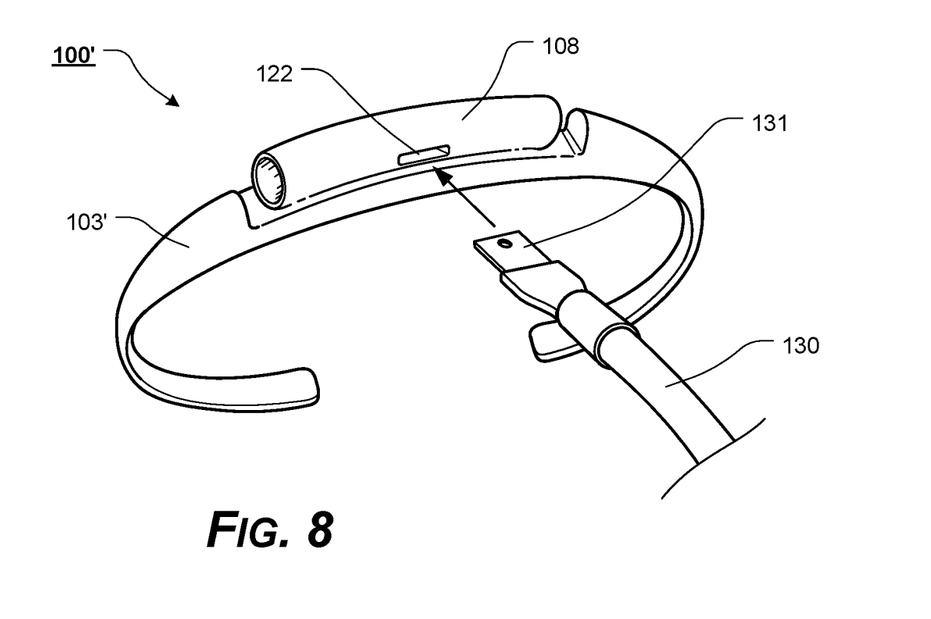
FIG. 8 illustrates a variant embodiment perspective view of certain elements or components of an exemplary embodiment of a therapeutic bracelet, according to the presently disclosed systems, methods, and/or apparatuses.
Figure 9:
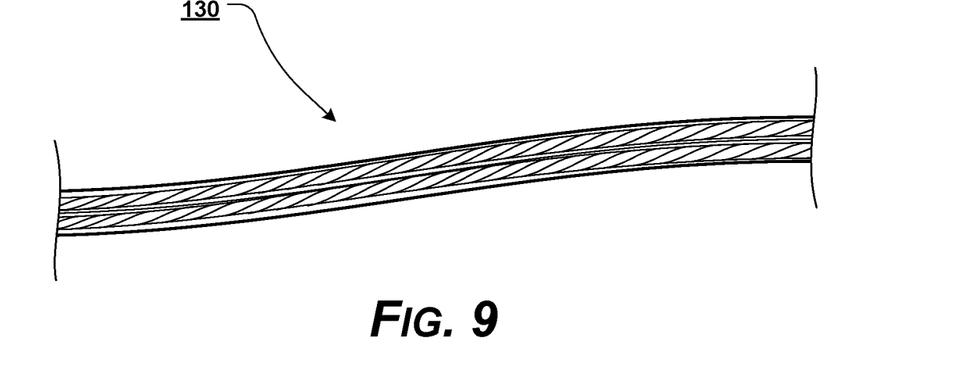
FIG. 9 illustrates a partial view of an exemplary connecting cord that may optionally be utilized in connection with an exemplary embodiment of the therapeutic bracelet, according to the presently disclosed systems, methods, and/or apparatuses.

Fixed or detachable male 121/131 and female 122/132 connectors may be attached or coupled to the bracelet body 103 and connecting cord 130, as illustrated, for example, in FIGS. 6 and 8. It should be appreciated that attachment or coupling of the electrical connector 120 and connecting cord 130 to the bracelet body 103 is done so as to ensure a robust connection of high electrical integrity. The connecting cord 130 may be conductively attached or coupled to the bracelet body 103 through a variety of configurations including different conductors, varying sizes, different profiles, etc.

In various exemplary embodiments, the connecting cord 130 is conductively attached or coupled to (or through) the bracelet body 103 or electrical connector 120 via a zip cord or other connecting cord 130 with the conductors separated, stripped, and soldered together to form a wired loop, through a short copper tube prior to forming the tube and affixing the tube and the connecting cord 130 to the bracelet body 103 creating the electrical connection. The length of stripping, the type of wire connection (solder, crimp, wrap, etc.), the position of the splice and the insertion attachment angles or wire positions within the formed electrical connector 120 may all be variants defined further or more specifically to promote effective electrical conductivity between the various components or elements.

Alternatively, the connecting cord 130 may be conductively attached or coupled directly to the bracelet body 103 through a variety of configurations including different conductors, varying sizes, different profiles, etc. Likewise, attachment methods could range from a general "epoxy" to very specific epoxies (e.g., marine grade epoxy) or other attachment methods such as soldering, brazing, etc. Certain surface preparations (e.g., scoring, etching, etc.) may be incorporated to enhance electrical conductivity, conductive performance, and/or durability between the connecting cord 130, the electrical connector 120, and/or the bracelet body 103.

The plug assembly 140 is optionally configured using a standard or modified North American-style three-pronged 110 VAC electrical plug 143, which is the typical plug 143 used for AC electrical connections in modern US homes. In these exemplary embodiments, as illustrated most clearly in FIGS. 10 and 11, the plug assembly 140 comprises a plug 143 having two pins or blades, a "live" pin or blade 145, a neutral pin or blade 147, and an earth/ground pin or blade 149.

Figure 10:
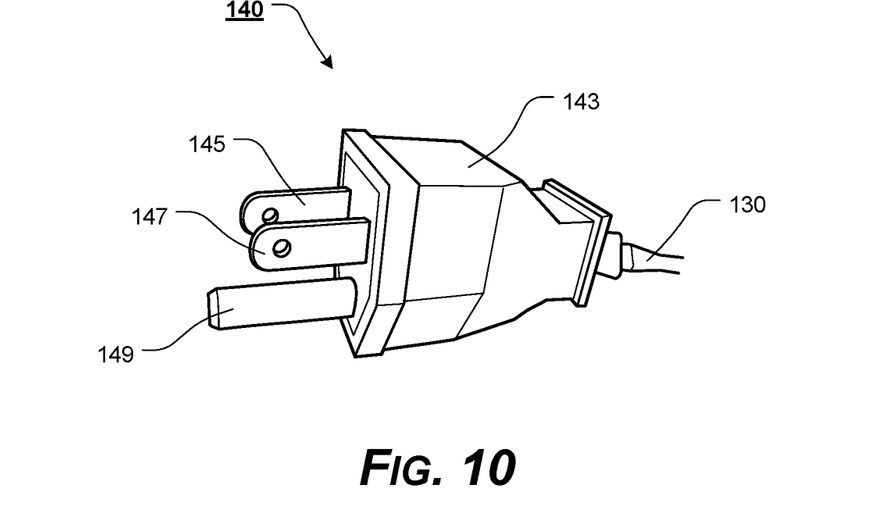
FIG. 10 illustrates a detailed view of an exemplary plug assembly, according to the presently disclosed systems, methods, and/or apparatuses.
Figure 11:
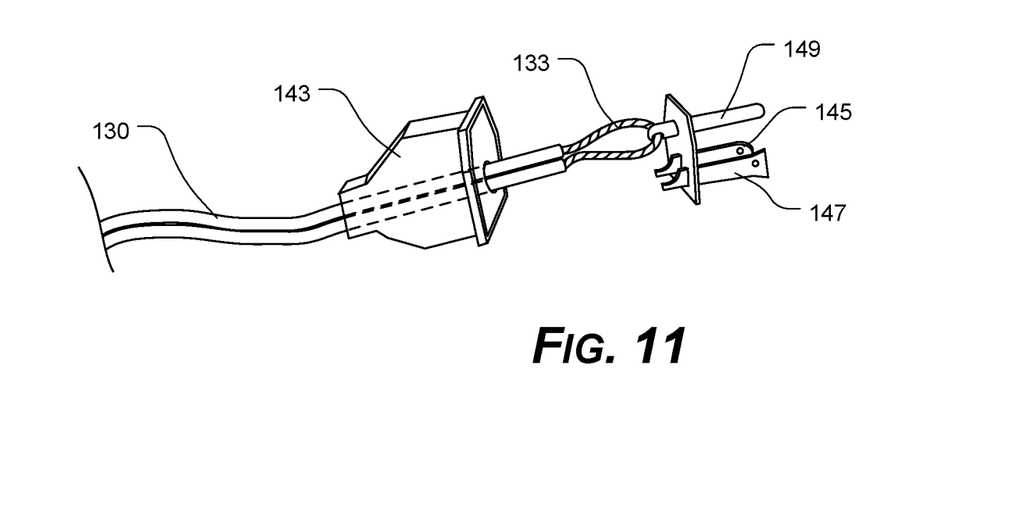
FIG. 11 illustrates a more detailed, partially exploded view of an exemplary plug assembly, according to the presently disclosed systems, methods, and/or apparatuses.

As further illustrated, the terminal ends of the conductive wire(s) 133 of the connecting cord 130 opposite the bracelet body 103 are stripped and electrically connected to the earth/ground pin or blade 149 of the electrical plug 143. In various exemplary embodiments, the electrical connection may optionally be made through a protective circuit breaker, such as, for example, a fuse 155. The neutral pin or blade 147 and "live" pin or blade 145 are not electrically connected to each other or to the conductive wire(s) 133 of the connecting cord 130 and are, in fact, electrically isolated from each other and from the conductive wire(s) 133 of the connecting cord 130. An exemplary embodiment of the electrical plug 143 may optionally include non-conductive "live" pin or blade 145 and the neutral pin or blade 147 made from one or more nonconductive materials, such as, for example, plastic.

Figure 12:
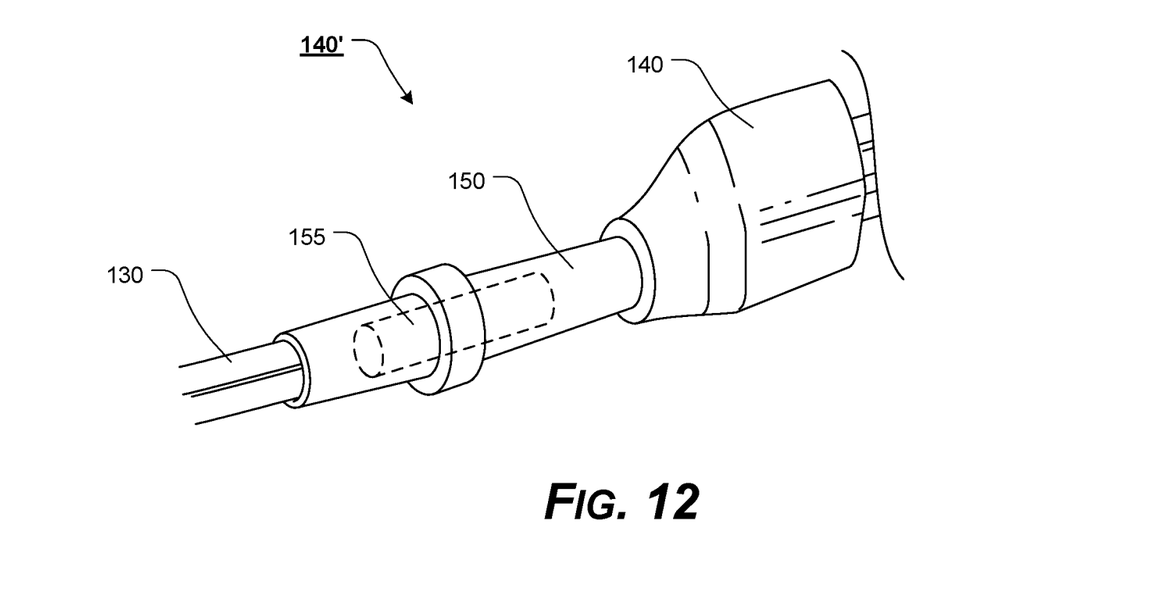
FIG. 12 illustrates a more detailed, partially exploded view of an exemplary plug assembly, including a protective fuse assembly, according to the presently disclosed systems, methods, and/or apparatuses.

Electrical connection of the connecting cord 130 to an optional protective fuse assembly 150 and, ultimately, to the earth/ground pin or blade 149 may be made through various means such as soldering, wrapping, crimping, screwing, etc. The neutral pin or blade 147 and "live" pin or blade 145 of the electrical plug 143 remain open (i.e., unattached or electrically isolated) and may be nonconductive or have sufficient clearance to prevent shorting to each other and/or to the ground pin or blade 149 under normal operating conditions. In various exemplary, nonlimiting embodiments, the neutral pin or blade 147 and the "live" pin or blade 145 may comprise non-conductive pins or blades. Alternatively, one of the neutral pin or blade 147 or the "live" pin or blade 145 may be removed from the electrical plug 143. Clearances may be enhanced through various means such as defined spacing, addition of insulators, etc. The electrical connection of the cord to the electrical plug 143 is fully enclosed (i.e., covered) to prevent contact exposure during use. The electrical connection may consist of a detachable connecting cord 130 to facilitate simple disassembly.

While the plug assembly 140 has been shown and described as using a standard North American-style three-pronged electrical plug 143, it should be appreciated that this is illustrative and not limiting. For example, the plug assembly 140 is designed to be capable of interfacing with any desired electrical outlet. Thus, the plug assembly 140 may be designed so as to interface with any electrical outlet, such as, for example any Type A, Type B, Type C, Type D, Type E, Type F, Type G, Type H, Type I, Type J, Type K, Type L, Type M, Type N, or Type O electrical outlet.

In each embodiment, the plug assembly 140 is configured such that if the electrical plug 143 is plugged into an electrical outlet, the earth/ground pin or blade 149 is electrically connected to the earth/ground of the electrical outlet. Thus, the therapeutic bracelet 100 is conductively attached or coupled to the earth/ground electrical system of the structure in which the electrical outlet is included and, ultimately, the earth/ground of the structures electrical system and/or the earth/ground of the associated power grid.

It should be appreciated that the plug assembly 140' corresponds to and operates similarly to the plug assembly 140, but is configured to be utilized in conjunction with the fuse assembly 150.

It should be appreciated that certain elements of the therapeutic bracelet 100 may be formed as an integral unit (such as, for example, the bracelet body 103 and the electrical connector 120). Alternatively, suitable materials can be used and sections or elements made independently and attached or coupled together, such as by adhesives, welding, screws, rivets, pins, or other fasteners, to form the various elements of the therapeutic bracelet 100.

It should also be understood that the overall size and shape of the therapeutic bracelet 100, and the various portions thereof, is a design choice based upon the desired functionality and/or appearance of the therapeutic bracelet 100.

FIG. 8 illustrates an alternative embodiment of the bracelet 100'. As illustrated, the bracelet 100' includes a bracelet body 103', having a recess formed to receive a conductive insert 108. In various exemplary embodiments, the conductive insert 108 includes an internal cavity formed so as to be filled or partially filled with a catalyst solution 110. The bracelet body 103' is electrically attached or coupled to the conductive insert 108, such that electrical contact between a user's skin and the bracelet body 103' provides electrical contact between the user and the conductive insert 108, and, in turn, the catalyst solution 110 contained within the conductive insert 108.

The conductive insert 108 is electrically attached or coupled to the connecting cord 130, utilizing a male spade connector 131 attached or coupled to the connecting cord 130 and a female receptacle 122 formed or attached in the conductive insert 108. It should be appreciated that the conductive insert 108 may be electrically attached or coupled to the connecting cord 130 using any of the methods described herein.

During use, the user's wrist (or other body part) is positioned within the partial aperture of the bracelet body 103. The bracelet body 103 is appropriately adjusted so as to make conductive contact with the user's skin. The plug assembly 140 is then manipulated such that the plug 143 is plugged into an appropriate, standard electrical outlet. By plugging the plug assembly 140 into the electrical outlet, the earth/ground pin or blade 149 makes electrical contact with the earth/ground provided through the electrical outlet. The "live" pin or blade 145 and/or neutral pin or blade 147 (if both are included) serve merely to provide proper alignment of the plug assembly 140 with the electrical outlet and additional frictional engagement to maintain the plug assembly 140 into position so as to continue electrical connection between the earth/ground pin or blade 149 and the earth/ground provided through the electrical outlet.

It should also be appreciated that a more detailed explanation of the power grid and electrical outlets, specific connection of the plug assembly 140 and earth/ground pin or blade 149 to an appropriate electrical outlet, and certain other items and/or techniques necessary for the implementation and/or operation of the various exemplary embodiments of the presently disclosed therapeutic bracelet 100 are not provided herein because such background information will be known to one of ordinary skill in the art. Therefore, it is believed that the level of description provided herein is sufficient to enable one of ordinary skill in the art to make and use the therapeutic bracelet 100, as have been described and in keeping with the present disclosure.

While the presently disclosed systems, methods, and/or apparatuses has been described in conjunction with the exemplary embodiments outlined above, the foregoing description of exemplary embodiments of the presently disclosed systems, methods, and/or apparatuses, as set forth above, are intended to be illustrative, not limiting and the fundamental disclosed systems, methods, and/or apparatuses should not be considered to be necessarily so constrained. It is evident that the presently disclosed systems, methods, and/or apparatuses are not limited to the particular variation set forth and many alternatives, adaptations modifications, and/or variations will be apparent to those skilled in the art.

Furthermore, where a range of values is provided, it is understood that every intervening value, between the upper and lower limit of that range and any other stated or intervening value in that stated range is encompassed within the presently disclosed systems, methods, and/or apparatuses. The upper and lower limits of these smaller ranges may independently be included in the smaller ranges and is also encompassed within the presently disclosed systems, methods, and/or apparatuses, subject to any specifically excluded limit in the stated range. Where the stated range includes one or both of the limits, ranges excluding either or both of those included limits are also included in the presently disclosed systems, methods, and/or apparatuses.

It is to be understood that the phraseology of terminology employed herein is for the purpose of description and not of limitation. Unless defined otherwise, all technical and scientific terms used herein have the same meaning as commonly understood by one of ordinary skill in the art to which the presently disclosed systems, methods, and/or apparatuses belongs.

In addition, it is contemplated that any optional feature of the inventive variations described herein may be set forth and claimed independently, or in combination with any one or more of the features described herein.

Accordingly, the foregoing description of exemplary embodiments will reveal the general nature of the presently disclosed systems, methods, and/or apparatuses, such that others may, by applying current knowledge, change, vary, modify, and/or adapt these exemplary, non-limiting embodiments for various applications without departing from the spirit and scope of the presently disclosed systems, methods, and/or apparatuses and elements or methods similar or equivalent to those described herein can be used in practicing the presently disclosed systems, methods, and/or apparatuses. Any and all such changes, variations, modifications, and/or adaptations should and are intended to be comprehended within the meaning and range of equivalents of the disclosed exemplary embodiments and may be substituted without departing from the true spirit and scope of the presently disclosed systems, methods, and/or apparatuses.

Also, it is noted that as used herein and in the appended claims, the singular forms "a", "and", "said", and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely", "only", and the like in connection with the recitation of claim elements or the use of a "negative" claim limitation(s).

What is claimed is:

1. A therapeutic bracelet, comprising:
   a bracelet body formed of an electrically conductive material and having one or more cavities formed therein;

a conductive catalyst solution contained within each of said one or more cavities;

an electrical connector electrically attached or coupled to said bracelet body;

a connecting cord electrically attached or coupled to said electrical connector; and a plug assembly, wherein said plug assembly includes a "live" pin or blade, a neutral pin or blade, and an earth/ground pin or blade, wherein said "live" pin or blade and said neutral pin or blade are electrically disconnected from said connecting cord and said earth/ground pin or blade, and wherein said earth/ground pin or blade is electrically connected to said connecting cord.

2. The therapeutic bracelet of claim 1, wherein each of said cavities is in fluid communication with each other cavity.

3. The therapeutic bracelet of claim 1, wherein said plug assembly is capable of interfacing with an electrical outlet.

4. The therapeutic bracelet of claim 1, wherein said plug assembly is capable of interfacing with a North American-style 110 VAC electrical outlet.

5. The therapeutic bracelet of claim 1, wherein said plug assembly is capable of interfacing with any Type B, Type D, Type G, Type H, Type I, Type J, Type K, Type L, Type M, Type N, or Type O electrical outlet.

6. The therapeutic bracelet of claim 1, wherein when 4 said electrical plug is plugged into a properly wired an electrical outlet, said earth/ground pin or blade is electrically connected to an earth/ground of said electrical outlet.

7. The therapeutic bracelet of claim 1, further comprising a fuse assembly attached or coupled between said connecting cord and said plug assembly.

8. A therapeutic bracelet, comprising:

a bracelet body formed of an electrically conductive material and having one or more cavities formed therein;

a conductive catalyst solution contained within each of said one or more cavities;

a connecting cord electrically attached or coupled to said bracelet body; and a plug assembly, wherein said plug assembly includes a "live" pin or blade, a neutral pin or blade, and an earth/ground pin or blade, wherein said "live" pin or blade and said neutral pin or blade are electrically disconnected from said connecting cord and said earth/ground pin or blade, and wherein said earth/ground pin or blade is electrically connected to said connecting cord.

9. The therapeutic bracelet of claim 8, wherein each of said one or more cavities is in fluid communication with each other cavity.

10. The therapeutic bracelet of claim 8, wherein said plug assembly is capable of interfacing with an electrical outlet.

11. The therapeutic bracelet of claim 8, wherein said plug assembly is capable of interfacing with a North American-style 110 VAC electrical outlet.

12. The therapeutic bracelet of claim 8, wherein said plug assembly is capable of interfacing with any Type B, Type C, Type D, Type G, Type H, Type I, Type J, Type K, Type L, Type M, Type N, or Type O electrical outlet.

13. The therapeutic bracelet of claim 8, wherein when 4 said electrical plug is plugged into a properly wired electrical outlet, said earth/ground pin or blade is electrically connected to an earth/ground of said electrical outlet.

14. The therapeutic bracelet of claim 8, further comprising a fuse assembly attached or coupled between said connecting cord and said plug assembly.

15. A therapeutic bracelet, comprising:

a bracelet body formed of an electrically conductive material and having at least one cavity formed therein;

a conductive catalyst solution contained within said at least one cavity;

a connecting cord electrically attached or coupled to said bracelet body; and a plug assembly, wherein said plug assembly includes a "live" pin or blade, a neutral pin or blade, and an earth/ground pin or blade, wherein said "live" pin or blade and said neutral pin or blade are nonconductive, and wherein said earth/ground pin or blade is electrically connected to said connecting cord.

16. The therapeutic bracelet of claim 15, wherein said at least one cavity is in fluid communication with each other cavity.

17. The therapeutic bracelet of claim 15, wherein said plug assembly is capable of interfacing with an electrical outlet.

18. The therapeutic bracelet of claim 15, wherein said plug assembly is capable of interfacing with any Type B, Type D, Type G, Type H, Type I, Type J, Type K, Type L, Type M, Type N, or Type O electrical outlet.

19. The therapeutic bracelet of claim 15, wherein when said electrical plug is plugged into a properly wired electrical outlet, said earth/ground pin or blade is electrically connected to an earth/ground of said electrical outlet.

20. The therapeutic bracelet of claim 15, further comprising a fuse assembly attached or coupled between said connecting cord and said plug assembly.

* * * * *